(12) United States Patent
Yin et al.

(10) Patent No.: US 12,736,419 B2
(45) Date of Patent: Sep. 15, 2026

(54) FORCE MEASURING DEVICE

(71) Applicant: SHL Medical AG, Zug (CH)

(72) Inventors: Ming-Ting Yin, Taoyuan City (TW); Chun Chang, Nacka Strand (SE); Yi-Ju Chen, Taoyuan City (TW)

(73) Assignee: SHL Medical AG, Zug (CH)

( * ) Notice: Subject to any disclaimer, the term of this patent is extended or adjusted under 35 U.S.C. 154(b) by 268 days.

(21) Appl. No.: 18/693,282

(22) PCT Filed: Sep. 14, 2022

(86) PCT No.: PCT/EP2022/075575
§ 371 (c)(1),
(2) Date: Mar. 19, 2024

(87) PCT Pub. No.: WO2023/052132
PCT Pub. Date: Apr. 6, 2023

(65) Prior Publication Data

US 2024/0393191 A1 Nov. 28, 2024

(30) Foreign Application Priority Data

Sep. 28, 2021 (EP) .................................... 21199420

(51) Int. Cl.
*G01L 5/22* (2006.01)
*G01L 1/04* (2006.01)
*A61M 5/315* (2006.01)

(52) U.S. Cl.
CPC ................ *G01L 1/042* (2013.01); *G01L 5/22* (2013.01); *A61M 5/31566* (2013.01); *A61M 2205/332* (2013.01)

(58) Field of Classification Search
CPC ....... G01L 1/042; G01L 5/22; A61M 5/31566
See application file for complete search history.

(56) References Cited

U.S. PATENT DOCUMENTS 4,653,329 A * 3/1987 Sagara .................. G01L 1/2293
338/42
5,510,812 A 4/1996 O'Mara
(Continued)

FOREIGN PATENT DOCUMENTS

CZ 32974 U1 * 6/2019 ............. G01N 37/00
DE 102004008487 A1 * 9/2005 ......... G01R 31/2891
(Continued)

OTHER PUBLICATIONS

International Search Report and Written Opinion for corresponding PCT application No. PCT/EP2022/075575, Dec. 20, 2022.

*Primary Examiner* — Jamel E Williams
(74) *Attorney, Agent, or Firm* — McDonnell Boehnen Hulbert & Berghoff LLP

(57) ABSTRACT

The present disclosure relates to a force measuring device comprising a spring module, and an electronic module, detachably mechanically connected to the spring module. The spring module comprises a test head defining an outer surface of the device, a spring seat, and a spring arranged between the test head and the spring seat, with a first end of the spring engaging the test head and a second end of the spring engaging the spring seat. The electronic module comprises a force sensor arranged in physical contact with the spring seat.

13 Claims, 4 Drawing Sheets

(56) References Cited

U.S. PATENT DOCUMENTS

| | | | | |
|---|---|---|---|---|
| 9,186,462 | B2 | 11/2015 | Lanzi | |
| 2015/0160080 | A1* | 6/2015 | Fujisawa | G01L 1/2231<br>73/862.627 |
| 2018/0238749 | A1* | 8/2018 | Doko | G01L 1/26 |

FOREIGN PATENT DOCUMENTS

| | | | | |
|---|---|---|---|---|
| EP | 2480863 | B1 * | 7/2013 | G01L 1/26 |
| EP | 3809980 | A1 | 4/2021 | |
| KR | 102365105 | B1 * | 2/2022 | G01L 5/0057 |
| WO | WO-2017070391 | A2 * | 4/2017 | G09B 23/285 |
| WO | 2018125887 | A2 | 7/2018 | |
| WO | WO-2019243597 | A1 * | 12/2019 | A61B 1/05 |

* cited by examiner

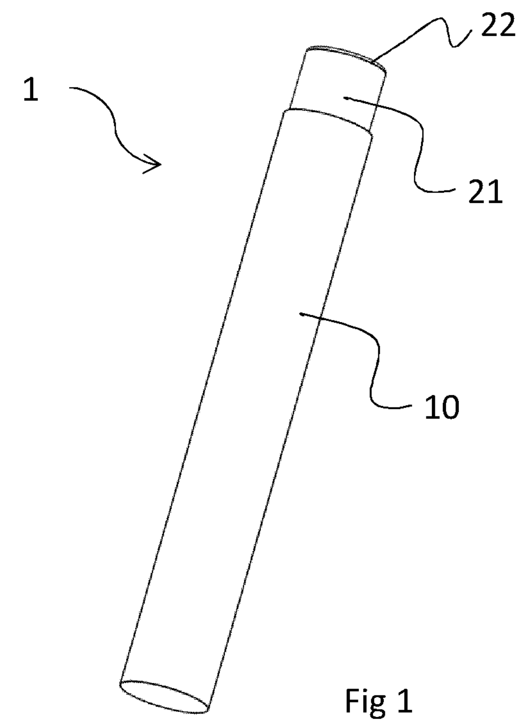
Fig 1
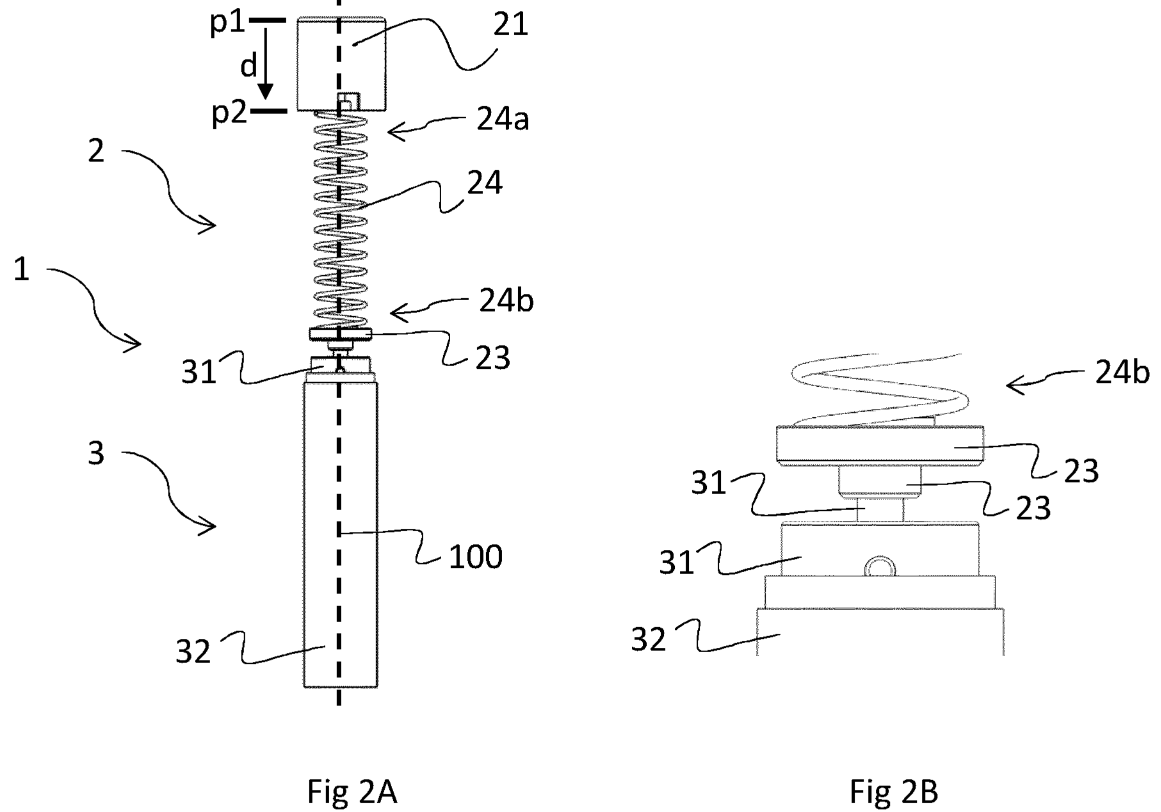
Fig 2A
Fig 2B

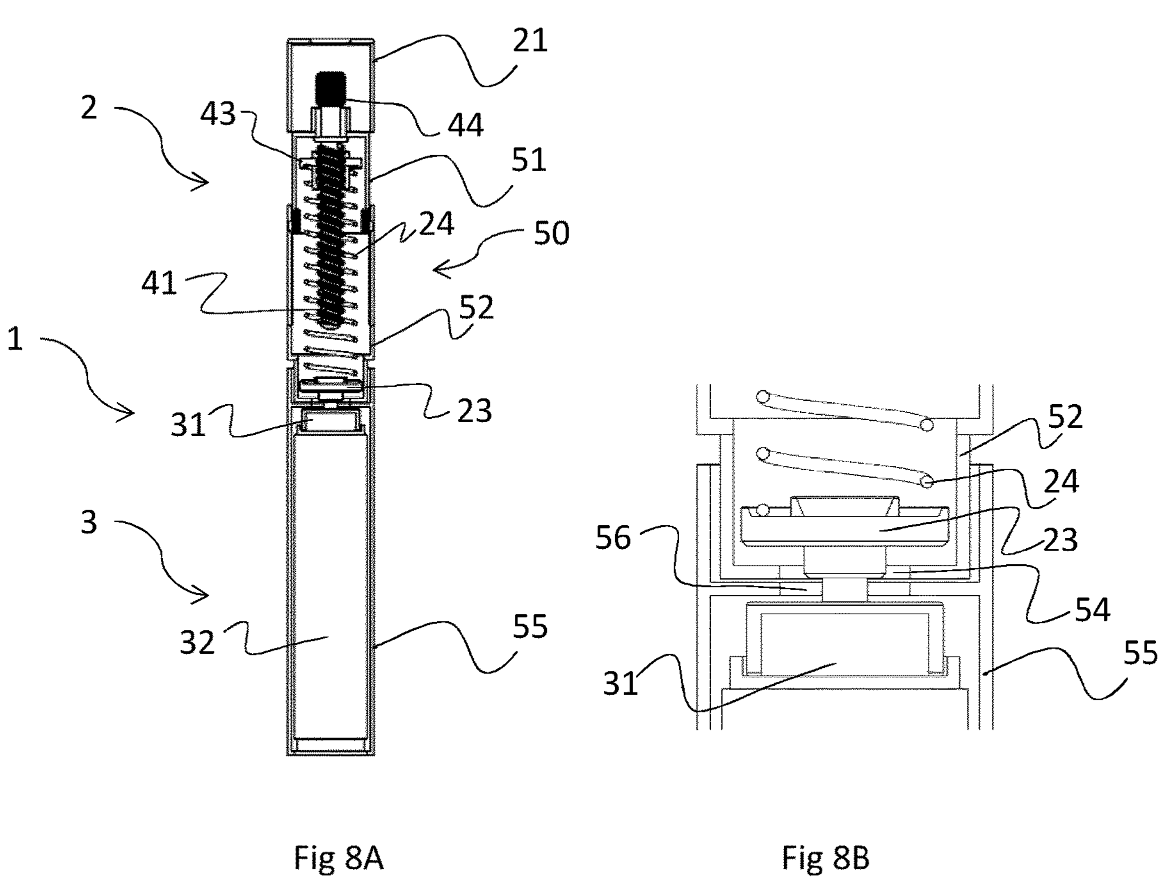
Fig 8A
Fig 8B
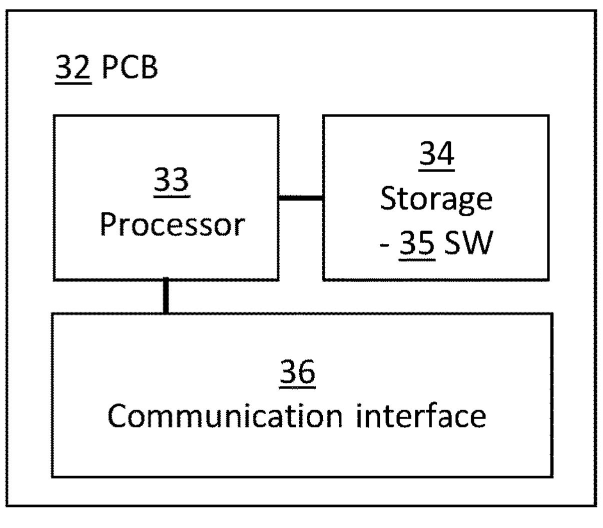
Fig 9
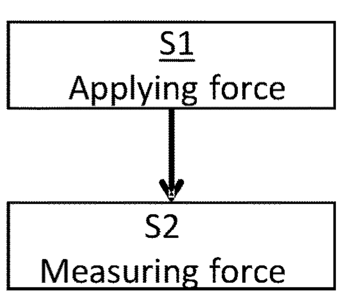
Fig 10

FORCE MEASURING DEVICE

CROSS-REFERENCE TO RELATED APPLICATIONS

The present application is a U.S. National Phase Application pursuant to 35 U.S.C. § 371 of International Application No. PCT/EP2022/075575 filed Sep. 14, 2022, which claims priority to European Patent Application No. 21199420.7 filed Sep. 28, 2021. The entire disclosure contents of these applications are herewith incorporated by reference into the present application.

TECHNICAL FIELD

The present disclosure relates to a force measuring device arranged for measuring a force applied to a medicament delivery device by a user.

BACKGROUND

When designing a medicament delivery device, it is desirable to know how a prospective user is able to handle the device. For instance, the force which the user typically can apply to a button or needle cap or the like may be desired input when designing the device.

WO 2020/182403 discloses a medicament delivery device development evaluation system comprising a dummy medicament delivery device comprising at least one force sensor configured to detect an external force applied to the dummy medicament delivery device. While this evaluation system works well for determining a force applied to the dummy device, it may be advantageous to provide a dummy device which mimics the medicament delivery device as well as possible in order to obtain the best data possible about how the user would handle the real device.

SUMMARY

It is an objective of the present invention to provide a force measuring device with improved ability to mimic a real medicament delivery device.

According to an aspect of the present invention, there is provided a force measuring device comprising a spring module, and an electronic module, detachably mechanically connected to the spring module. The spring module comprises a test head defining an outer surface of the device, a spring seat, and a spring arranged between the test head and the spring seat, with a first end of the spring engaging the test head and a second end of the spring engaging the spring seat. The electronic module comprises a force sensor arranged in physical contact with the spring seat. The spring module further comprising a spring force adjustment arrangement arranged to adjust an accumulated force of the spring.

According to another aspect of the present invention, there is provided a force measuring device comprising a spring module, and an electronic module, detachably mechanically connected to the spring module. The spring module comprises a test head defining an outer surface of the device, a spring seat, and a spring arranged between the test head and the spring seat, with a first end of the spring engaging the test head and a second end of the spring engaging the spring seat. The electronic module comprises a force sensor arranged in physical contact with the spring seat.

According to another aspect of the present invention, there is provided a method for measuring an external force applied by a user to the test head of an embodiment of the force measuring device of the present disclosure. The method comprises the user applying a force to the test head, and the sensor measuring a first part of the applied force, said first part being transmitted to the spring seat via the spring.

According to another aspect of the present invention, there is provided a kit comprising a plurality of spring modules, each in accordance with the present disclosure, the spring of each spring module having a respective different spring constant, and an electronic module in accordance with the present disclosure, the electronic module being detachably mechanically connectable to each of the spring modules to bring the force sensor of the electronic module into physical contact with the spring seat of the spring module.

By means of the spring, the force measuring device can provide movement and force feedback to the user which to the user may feel more like a real medicament delivery devise. The measured applied force may then better match the force the user would apply to the real device.

By the electronic module being detachable from the spring module, either of the spring module and the electronic module may be easily exchanged. For instance, the spring module may be exchanged for another spring module with a spring having another spring constant, allowing the force range of the spring to be adapted to different applications of the force measuring device while using the same electronic module. A kit comprising a plurality of spring modules, each having a spring with a respective different spring constant, and a single electronic module, can conveniently be provided and used.

In some embodiments of the present invention, the spring is a compression spring, a tension spring or a torsion spring. In some embodiments, the spring is a compression spring, which may be preferred for some applications. In some embodiments, the spring is a coils spring, which may be preferred for some applications.

In some embodiments of the present invention, the test head is movable between a first end position and a second end position during elastic deformation of the spring. In some embodiments, the spring module further comprises a rigid element fixed in relation to the test head and arranged to be in contact with the spring seat at the second end position. In some embodiments, the rigid element is a rod-shaped component.

In some embodiments of the present invention, the spring module further comprises a spring force adjustment arrangement arranged to adjust an accumulated force of the spring. In some embodiments, the spring force adjustment arrangement is arranged to adjust a longitudinal extension of the spring between the test head and the spring seat. In some embodiments, the spring force adjustment arrangement comprises a lead screw axially fixed in relation to the test head (21), and a spring cap directly engaged with the first end of the spring, the spring cap being screwed onto the lead screw and being axially movable and rotationally fixed in relation to the test head.

In some embodiments of the present invention, the spring module comprises a head joint fixed in relation to the test head and a spring cover fixed in relation to the spring seat. In some embodiments, the spring cover and the head joint are telescopically arranged, allowing the head joint to be movable in relation to the spring cover in a longitudinal direction. In some embodiments, the test head is detachably connected to the head joint, e.g. by means of a bayonet connector, a screw thread or a snap-fit connector.

In some embodiments of the present invention, the device comprises a rear housing and a front housing. In some embodiments, the electronic module is fully or at least partly arranged within the rear housing. Additionally or alternatively, in some embodiments, the spring module is fully or at least partly arranged within the front housing. In some embodiments, an opening is arranged in a wall of the rear housing and a counter opening is arranged in a wall of the front housing. In some embodiments, the force sensor is in physical contact with the spring seat though the opening and the counter opening. Additionally or alternatively, in some embodiments, the rear housing is detachably connected to the front housing by means of a bayonet connector, a screw thread connector or a snap-fit connector. In some embodiments, the front housing is formed by the head joint and the spring cover. In some embodiments, the counter opening is arranged in a wall of the spring cover.

In some embodiments of the present invention, the device further comprises an outer shell extending along a longitudinal axis of the device. In some embodiments, the spring seat is arranged within the outer shell. Additionally or alternatively, in some embodiments, the test head is partially arranged within the outer shell. In some embodiments, the outer shell is shaped as a medicament delivery device, e.g. an autoinjector, pen injector and/or inhaler. In some embodiments, the test head is telescopically arranged in relation to the outer shell. In some embodiments, the electronic module is fully or at least partly arranged within the outer shell. In some embodiments, all of or at least a part of the rear housing is arranged within the outer shell. Additionally or alternatively, in some embodiments, all of or at least a part of the front housing is arranged within the outer shell.

In some embodiments of the present invention, the external force applied to the test head is a press force, a tensile force or a torque. In some embodiments, the force is a press force applied in a direction towards the spring seat, which may be preferred for some applications.

In some embodiments of the present invention, the test head is moved from a first end position to a second end position by the force applied to the test head, during elastic deformation of the spring. In some embodiments, when the test head has reached the second end position, the measuring further comprises measuring a second part of the applied force, said second part being transmitted to the spring seat via a rigid element, e.g. a rod-shaped element such as the lead screw, contacting the spring seat, said rigid element being fixed in relation to the test head.

It is to be noted that any feature of any of the aspects may be applied to any other aspect, wherever appropriate. Likewise, any advantage of any of the aspects may apply to any of the other aspects. Other objectives, features and advantages of the enclosed embodiments will be apparent from the following detailed disclosure, from the attached dependent claims as well as from the drawings.

Generally, all terms used in the claims are to be interpreted according to their ordinary meaning in the technical field, unless explicitly defined otherwise herein. All references to "a/an/the element, apparatus, component, means, step, etc." are to be interpreted openly as referring to at least one instance of the element, apparatus, component, means, step, etc., unless explicitly stated otherwise. The steps of any method disclosed herein do not have to be performed in the exact order disclosed, unless explicitly stated. The use of "first", "second" etc. for different features/components of the present disclosure are only intended to distinguish the features/components from other similar features/components and not to impart any order or hierarchy to the features/components.

BRIEF DESCRIPTION OF THE DRAWINGS

Embodiments will be described, by way of example, with reference to the accompanying drawings, in which:

FIG. 1 is a schematic perspective view of a force measuring device having an outer shell, in accordance with some embodiments of the present invention.

FIG. 2A is a schematic side view of a force measuring device, in accordance with some embodiments of the present invention.

FIG. 2B is an enlargement of a detail of FIG. 2A, showing the interface between the spring module and the electronic module.

FIG. 8A is a schematic view in longitudinal section of a force measuring device, e.g. as in FIG. 7, in accordance with some embodiments of the present invention.

FIG. 8B is an enlargement of a detail of FIG. 8A, showing the interface between the spring module and the electronic module.

FIG. 9 is a schematic block diagram of the PCB of the electronic module, in accordance with some embodiments of the present invention.

FIG. 10 is a schematic flow chart of a method in accordance with some embodiments of the present invention.

DETAILED DESCRIPTION

Figures 3, 4, 5:
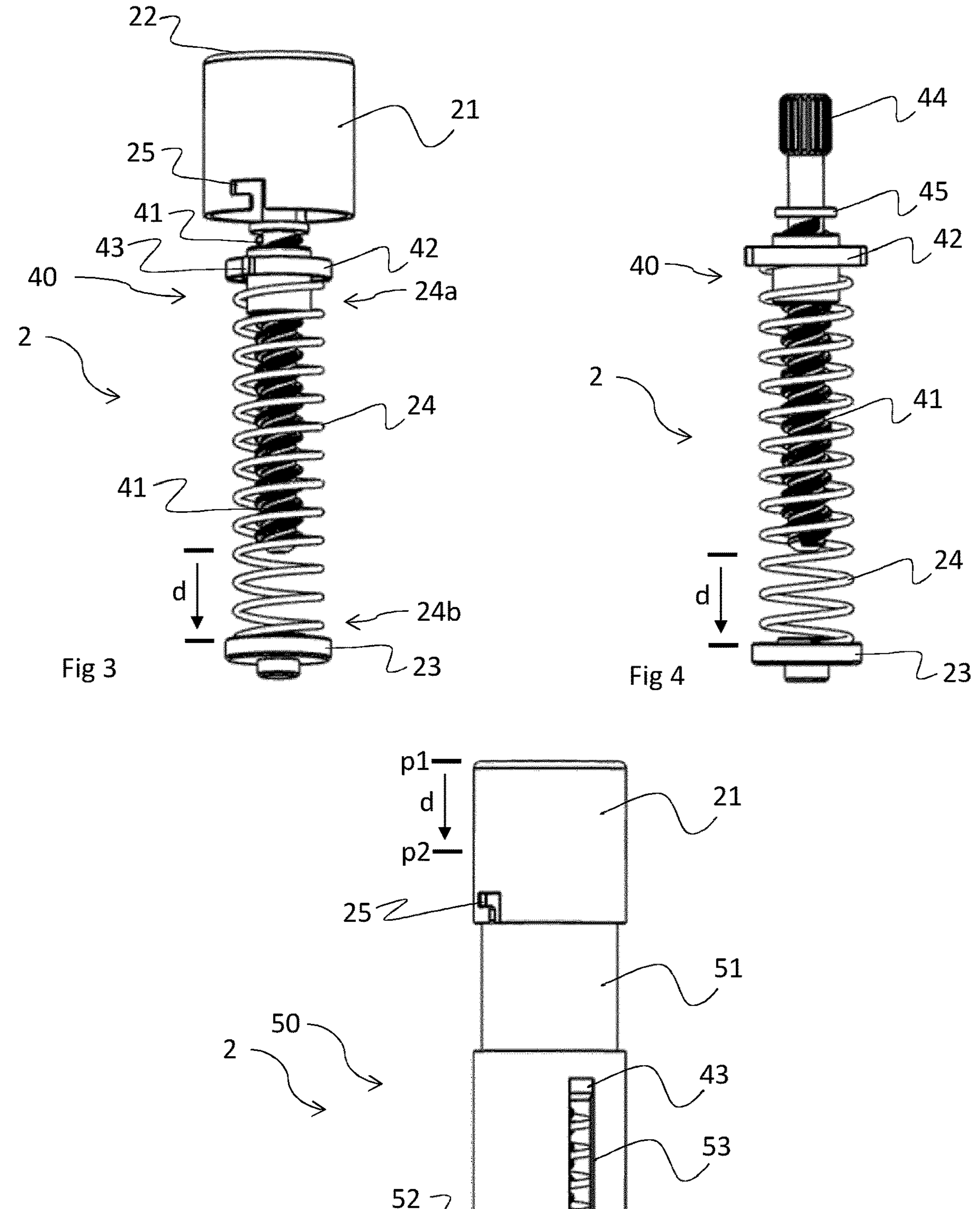
FIG. 3 is a schematic side view of a spring module comprising a spring force adjustment arrangement, in accordance with some embodiments of the present invention.
FIG. 4 is a schematic side view of a spring module, e.g. as in FIG. 3, with the test head removed, in accordance with some embodiments of the present invention.
FIG. 5 is a schematic side view of a spring module, e.g. as in FIG. 3 or 4, with a front housing, in accordance with some embodiments of the present invention.

Embodiments will now be described more fully hereinafter with reference to the accompanying drawings, in which certain embodiments are shown. However, other embodiments in many different forms are possible within the scope of the present disclosure. Rather, the following embodiments are provided by way of example so that this disclosure will be thorough and complete, and will fully convey the scope of the disclosure to those skilled in the art. Like numbers refer to like elements throughout the description.

FIG. 1 illustrates an embodiment of a force measuring device 1 in accordance with some embodiments of the present invention. The device comprises a test head 21 which defines an outer, outer surface 22 of the device 1. By the surface 22 being outer/external, a user is enabled to interact with the surface, typically by applying an external force to the surface and thus to the test head. That the force is external here implies that the force originates from outside of the device 1, e.g. applied by a human user.

The applied force may be any type of force, applied in any direction. For instance, the force may be a press force applied by the user pressing down on the surface 22 of the test head 21, or a tensile force applied by a user pulling on the test head 21 when holding it at its surface 22, or a torque applied by a user twisting the test head 21 when holding it at its surface 22. Herein, the embodiments of the invention will be discussed with a press force used as an example, which may be preferred in some embodiments e.g. when the device 1 mimics an autoinjector, pen injector or inhaler.

In some embodiments of the present invention, the device 1 comprises an outer shell 10. The outer shell may protect the movable and/or electronic parts of the device from external disruption or pollution. The outer shell may extend along the longitudinal axis 100 (see FIG. 2) of the device, e.g. partly or fully encompassing the electronic module and/or partly or fully encompassing the spring module of the device (with the exception of the part of the test head 21 defining the outer surface 22. Specifically, in some embodiments, the spring seat 23 (see FIG. 2A) may be arranged within the outer shell 10, e.g. protecting the spring seat from other external forces than the force applied by the user. In embodiments of the device 1 comprising a rear housing 55 and/or a front housing 50 (see FIG. 7), all of, or at least a part of, the rear housing 55 may be arranged within the outer shell 10, and/or all of, or at least a part of, the front housing 50 may be arranged within the outer shell 10.

In some embodiments, the outer shell 10 is shaped as a medicament delivery device, e.g. an autoinjector, pen injector and/or inhaler, which may further improve the real-feel for the user of the device 1. In some embodiments, the outer shell 10 may be detachably arranged, allowing the outer shell 10 to be exchanged for another outer shell, e.g. having another shape mimicking another medicament delivery device.

The test head 21 may be telescopically arranged in relation to the outer shell 10, e.g. movable along a longitudinal axis 100 (see FIG. 2A) of the device in relation to the outer shell 10. In the example of the figure, the test head 21 is concentrically arranged partly extending inside of the outer shell. Thus, the test head 21 may be partly arranged within the outer shell 11, while still defining an outer surface 22 accessible to a user.

FIG. 2A illustrates some embodiments of the device 1. No outer shell 10 is shown, but an outer shell may be used as discussed above. The force measuring device 1 comprises a spring module 2 and an electronic module 3, arranged in contact with each other along a longitudinal axis 100 of the device 1.

The spring module 2 comprises the test head 21, a spring seat 23 and a spring 24 arranged between the test head 21 and the spring seat 23. A first end 24*a* of the spring 24 directly or indirectly engages the test head 21, e.g. such that the test head 21 is fixed in relation to the first end 24*a*. Thus, the spring 24 is affected by a force is applied to the test head 21. A second end 24*b* of the spring 24 directly or indirectly engages the spring seat 23. Typically, the spring seat 23 is in direct contact with the second end 24*b* of the spring 24, e.g. by the spring 24 being fastened to the spring seat 23 or by the spring 24 being pressed against the spring seat 23.

By the spring 24 engaging both the test head 21 and the spring seat 23, at least a part of an external force applied to the test head 21, e.g. a press force, a tensile force and/or a torque, preferably a press force, can be transmitted to the spring seat 23 via the spring 24. A press force could be applied towards the spring seat 23, along the longitudinal axis 100, a tensile force could be applied away from the spring seat 23, along the longitudinal axis 100, and a torque could be applied in a plane perpendicular to the longitudinal axis 100. Thus, the spring 24 may be a compression spring, a tension spring or a torsion spring. In some embodiments, as also exemplified in the figures, the spring 24 is a compression spring, typically arranged for a press force applied to the test head 21. In some embodiments, as also exemplified in the figures, the spring 24 is a coil spring. An advantage of a coil spring is that it may fit, also during elastic deformation, within a cover of the device 1 arranged along the longitudinal axis 100, e.g. the outer shell 10 and/or the font housing 50.

It follows that, in response to an external force being applied to the test head 21, provided that said external force overcomes any pre-accumulated force of the spring (also called pre-tension or biasing), the test head 21 may be movable (in relation to e.g. the spring seat 23) from a first (resting) end position p1 during elastic during elastic deformation of the spring 24, thus providing movement and force feed-back to the user applying the external force. In some embodiments, the test head 21 is movable a distance d from the first end position p1 towards a second end position p2, at which second position a structural limitation of the spring module 2 prevents further movement of the test head in response to the external force applied. Such a structural limitation may be by a rigid element (e.g. in the form of a lead screw 41, see FIG. 3) which is fixed in relation to the test head 21 and which physically contacts the spring seat 23 when the test head 21 is in the second end position, said physical contact thus preventing further axial movement of the test head. The rigid element may be a rod-shaped component, typically extending in a longitudinal direction from the test head towards the spring seat.

The electronic module 3 comprises the force sensor 31 which is arranged in physical contact with the spring seat 23, allowing the force sensor 31 to measure at least a part of the external force applied to the test head, as transmitted via the spring 24 and (optionally) also via any other structural element of the spring module 2 as further discussed below. The electronic module may also comprise means for handling and/or processing measurement signals from the force sensor 31, e.g. comprising a Printed Circuit Board (PCB) 32.

FIG. 2B is an enlargement of a part of FIG. 2A, showing the interface between the spring module 2 and the electronic module 3 where the force sensor 31 is in physical contact with the spring seat 23, enabling forces to be transmitted from the spring seat to the force sensor allowing the force sensor to detect and measure at least a part of the force transmitted to the spring seat.

FIG. 3 illustrates some embodiments of the spring module 2 comprising a spring force adjustment arrangement 40 arranged to adjust an accumulated force of the spring 24. By means of the spring force adjustment arrangement 40, a force can be pre-accumulated in the spring 24 while the test head 21 is in its resting end position p1, before the external force is applied by the user. Thus, the external force needed, and feedback force provided, can be adjusted within an operating range of the spring depending on the spring constant of the spring. For instance, the spring force adjustment arrangement 40 may be arranged to adjust a longitudinal extension of the spring 24 between the test head 21 and the spring seat 23, typically without changing the distance between the test head 21 and the spring seat 23.

In some embodiments of the present invention, the spring force adjustment arrangement 40 comprises a lead screw 41 which is axially fixed in relation to the test head 21, and a spring cap 42 directly engaged with the first end 24*a* of the spring 24, the spring cap being screwed onto the lead screw 41 and being axially movable and rotationally fixed in relation to the test head 21. The lead screw is fixed in relation to the test head and is typically oriented to axially extend longitudinally towards the spring seat 23. Thus, when the lead screw 41 is turned in relation to the rotationally fixed spring cap, the spring cap 42 is guided by the male thread to move axially towards or away from the spring seat 23, thus adjusting the longitudinal extension of the spring 24. The spring cap 42 may be engaged with the first end 24*a* of the spring 24 by being pressed against said first end 24*a*, e.g. if the spring is a compression spring which is pre-compressed between the spring cap 42 and the spring seat 23 to provide the accumulated force, or by being fastened to said first end 24*a*, e.g. if the spring is a tension spring which is pre-tensed between the spring cap 42 and the spring seat 23 to provide the accumulated force.

As mentioned above, the lead screw 41, which is axially fixed in relation to the test head, may form a rigid element which stops axial movement of the test head 21 towards the spring seat 23 at the second end position p2 after having been moved the distance d by making physical contact with the spring seat at said second end position p2 of the test head 21.

The lead screw may at least partly extend axially within the spring, towards the spring seat 23, especially when the spring is a coil spring, as shown in FIG. 3.

FIG. 4 illustrates that the lead screw 41 may comprise a force adjusting knob 44, for facilitating turning of the lead screw. The force adjusting knob 44 may typically be provided at an end of thew lead screw which is longitudinally extending beyond the spring 24. The test head 21 may be detachably fitted over (and around) the knob 44, fixing the test head in relation to the lead screw.

The test head 21 may be fixed in relation to the lead screw 41 e.g. by being attached directly to the lead screw and/or by being connected to a front housing 50, e.g. as shown in FIG. 5.

In some embodiments of the present invention, the spring module 2 is arranged at least partly within a front housing 50. The front housing may protect e.g. the spring seat 23 and/or the spring 24 from external disturbance. The front housing 50 may also mechanically connect to the test head 21 and/or to the spring cap 42. Thus, the test head 21 may be held in place in the device 1 at least partly by being attached to the front housing by a connector 25. In some embodiments, the test head 21 is detachably connected to the front housing 50, e.g. to a head joint 51 thereof, e.g. by means of a connector 25, such as a bayonet connector (as in the example of FIG. 5), a screw thread or a snap-fit connector.

A function of the front housing 50 may be to fix the test head 21 in relation to the spring cap when in its resting end position p1. For instance, the front housing may be arranged to restrict the longitudinal extension of the spring 24, e.g. in cooperation with the spring force adjustment arrangement 40, facilitating pre-accumulation of force in the spring 24 by means of the spring force adjustment arrangement 40. In the example of FIG. 5, where a compression spring is used, this is achieved by the spring seat 23 being arranged within the front housing 50, e.g. within the spring cover 52 thereof, and the spring cap 42 being mechanically connected to the front housing 50, e.g. to the spring cover 52 thereof. The front housing 50, e.g. the spring cover 52 thereof, may thus limit the maximum longitudinal extension of the spring 24 by the front housing, e.g. the spring cover, being rigid or having a limited maximum longitudinal extension.

Regarding the spring cap 42, it may be provided with a radially protruding tooth 43, or other outwards extending protrusion, which may be in mesh with a longitudinal groove or slit 53 of the front housing 50, e.g. of a spring cover 52 thereof, preventing the spring cap 42 from rotating while allowing the spring cap to move axially (i.e. in a longitudinal direction) along the longitudinal extension of the groove or slit 53. This is one example of how to realize the spring cover being axially movable and rotationally fixed in relation to the test head 21, especially when the test head is also attached to the front housing.

Additionally, the front housing 50 may engage the lead screw 41 to prevent it from axial movement while it is being turned, e.g. being turned by means of the force adjusting knob 44 extending outside of the front housing. The front housing 50, e.g. a head joint 51 thereof, may engage the lead screw to prevent it from axial movement e.g. by meshing with a radially extending flange 45, or other radially extending protrusion or ridge, of the lead screw. The flange may conveniently be positioned at a part of the lead screw which axially extends beyond the spring 24, e.g. at a part of the lead screw between the spring cap 42 and the force adjusting knob 44. Thus, the front housing may limit the maximum longitudinal extension of the spring module 2, e.g. as measured between the test head 21 and the spring seat 23, by the front housing being rigid or having an otherwise limited maximum longitudinal extension.

In some embodiments, the front housing 50 comprises a head joint 51 which is fixed in relation to the test head 21, e.g. by means of the connector 25 as mentioned above.

In some embodiments, the front housing 50 comprises a spring cover 52 which is fixed in relation to the spring seat 23, e.g. by being mechanically connected to the electronic module 3.

In case the front housing 50 comprises a head joint 51, e.g. fixed in relation to the test head 21, and a spring cover 52, e.g. fixed in relation to the spring seat 23, the spring cover 52 and the head joint 51 may conveniently be telescopically arranged, allowing the head joint to be movable in relation to the spring cover in a longitudinal direction, but typically not rotationally movable in relation to the spring cover. That the head joint 51 and the spring cover 52 are telescopically arranged may imply that they are concentrically arranged at least partly overlapping and slidably connected to each other. Typically, the telescopic connection has a stopper functionality preventing the head joint 51 and the spring cover 52 from separating from each other in the longitudinal direction, thus also providing the limited maximum longitudinal extension of the front housing 50.

Figures 6, 7:
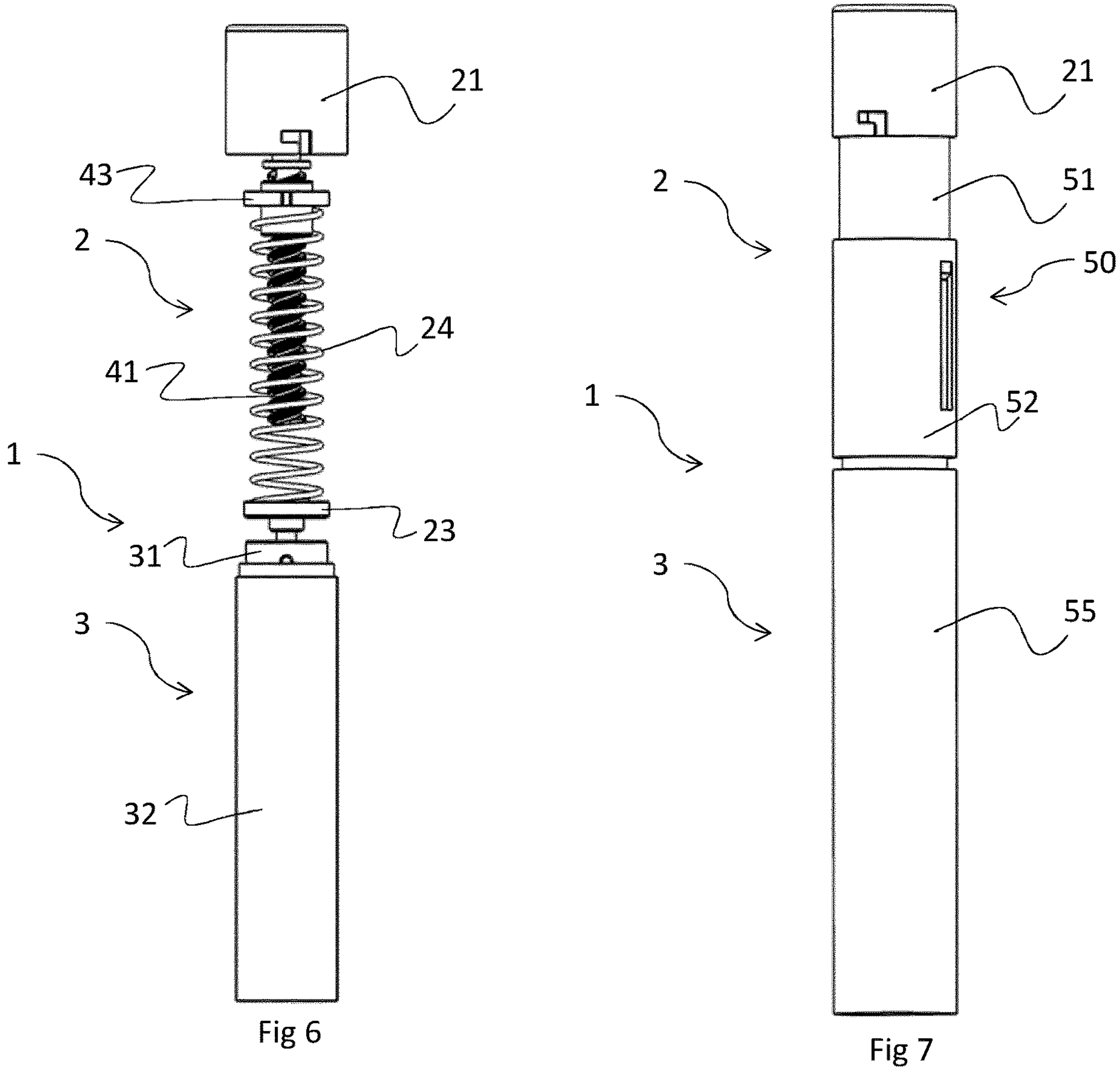
FIG. 6 is a schematic side view of a force measuring device comprising a spring force adjustment arrangement, in accordance with some embodiments of the present invention.
FIG. 7 is a schematic side view of a force measuring device, e.g. as in FIG. 6, comprising a front housing and a rear housing, in accordance with some embodiments of the present invention.

FIG. 6 illustrates an embodiment of the device 1, comprising a spring module 2 comprising a spring force adjustment arrangement 40, e.g. as discussed above in relation to FIGS. 3-5. The force sensor 31 is here in direct physical contact with the spring seat 23, allowing the force sensor to sense and measure at least a part of a force transmitted to the spring seat, e.g. via the spring 24 and/or via the lead screw 41 (especially when the test head 21 is held in its second end position p2).

FIG. 7 illustrates an embodiment of the device 1 comprising both a front housing 50 and a rear housing 55. The device may otherwise be as illustrated in e.g. FIG. 6, but with the electronic module 3 arranged in the rear housing 55 and the spring module 2 at least partly arranged in the front housing, e.g. as discussed in relation to FIG. 5.

Thus, in some embodiments, the device 1 comprises a rear housing 55. In some embodiments the electronic module 3 is fully or at least partly arranged within the rear housing 55.

Additionally or alternatively, in some embodiments, the device 1 comprises a front housing 50. In some embodiments, the spring module 2 is fully or at least partly arranged within the front housing 50, though the test head 21 still defines an outer surface of the device 1, e.g. by longitudinally extending at least partly beyond the front housing 50 (e.g. as shown in FIG. 7). In some embodiments, the front housing 50 is formed by the head joint 51 and the spring cover 52, as discussed herein.

In some embodiments, the rear housing 55 is detachably mechanically connected to the front housing 50 by means of a mechanical connector, e.g. a bayonet connector, a screw thread connector or a snap-fit connector.

It is noted that the device 1 may comprise an outer shell 10, e.g. as discussed above, which may be arranged to define an outer surface of the device, e.g. of any of the embodiments of FIGS. 6 and 7. The outer shell 10 may cover all or part of, the spring module 2 and/or the electronic module 3, typically extending along the longitudinal axis 100 of the device 1. In some embodiments, the spring seat 23 is arranged within the outer shell 10. In some embodiments, the test head 21 is partially arranged within the outer shell 10. Advantageously, the outer shell 10 is shaped as a medicament delivery device, e.g. an autoinjector, pen injector and/or inhaler. In some embodiments, the test head 21 is telescopically arranged in relation to the outer shell 10, e.g. by the test head axially and concentrically partly extending within the outer shell 10. In some embodiments, all of the rear housing 55 and all of or at least a part of the front housing 50 are arranged within the outer shell 10.

FIGS. 8A and 8B show a longitudinal section of an embodiment of the device 1. In this embodiment, the electronic module 3 is arranged within a rear housing 55, and the spring 24 and the spring seat 23 are arranged within a front housing 50, consisting of the telescopically arranged spring cover 52 and head joint 51, while the test head 21 is arranged outside of the front housing 50 in the axial/longitudinal direction.

As more clearly shown in FIG. 8B, the rear housing 55 is provided with an opening 56 and the front housing 50 (here the spring cover 52) is provided with a corresponding counter opening 54. The opening 56 and counter opening 54 overlap to provide a longitudinal open passage between the front housing 50 and the rear housing 55, through which passage the force sensor 31 can contact the spring seat 23. In the example of FIGS. 8A and 8B, the force sensor contacts the spring seat 23 such that the spring seat is lifted somewhat in the longitudinal direction such that the spring seat is not in contact with the wall of the front housing in which the counter opening 54 is provided. Thus, force transmitted to the spring seat is not, or at least to a lesser degree, taken up by the front cover, the force instead being transmitted to the force sensor, allowing the force sensor to sense and measure it.

FIG. 9 schematically illustrates an embodiment of a PCB 32 of the present disclosure. The PCB 32 comprises processing circuitry 33 e.g. a central processing unit (CPU). The processing circuitry 33 may comprise one or a plurality of processing units in the form of microprocessor(s). However, other suitable devices with computing capabilities could be comprised in the processing circuitry 33, e.g. an application specific integrated circuit (ASIC), a field programmable gate array (FPGA) or a complex programmable logic device (CPLD). The processing circuitry 33 is configured to run one or several computer program(s) or software (SW) 35 stored in a storage 34 of one or several storage unit(s) e.g. a memory. The SW 35 may enable the device 1 to perform an embodiment of the method of the present disclosure when the SW is run on the processing circuitry 33. The storage unit may be regarded as a computer readable means, forming a computer program product together with the SW 35 stored thereon as computer-executable components and may e.g. be in the form of a Random Access Memory (RAM), a Flash memory or other solid state memory, or a hard disk, or be a combination thereof. The processing circuitry 33 may also be configured to store data, e.g. information about measurements by the force sensor 31, in the storage 34, as needed. In some embodiments, the PCB 32 may further comprise a communication interface 36, e.g. a wireless or wired, preferably wireless, communication interface, e.g. for transmitting signals comprising information about measurements by the force sensor 31.

FIG. 10 illustrates some embodiments of the method of the present disclosure. The method is for measuring an external force applied by a user to the test head 21 of an embodiment of the force measuring device 1 of the present disclosure. The method comprises the user applying S1 an external force to the test head 21), and the sensor 31 measuring S2 a first part of the applied S1 force, said first part being transmitted to the spring seat 23 via the spring 24.

In some embodiments of the present invention, the external force applied S1 by the user is a press force, a tensile force or a torque, e.g. a press force applied in a direction towards the spring seat 23.

In some embodiments of the present invention, the test head 21 is moved from the first (resting) end position p1 towards and/or to the second end position p2 by the force applied S1 to the test head, during elastic deformation of the spring 24. The applied S1 force may be strong enough to move the test head 21 the whole distance d to the second end position p2, or it may be too weak to achieve this, only moving the test head a part of the distance d towards the second end position or not at all being able to move the test head from the first end position p1. In some embodiments, when the test head 21 has reached the second end position p2, the measuring S2 further comprises measuring a second part of the applied S1 force, said second part being transmitted to the spring seat 23 via a rigid element 41, e.g. the lead screw 41, making physical contact with the spring seat 23, said rigid element being fixed in relation to the test head.

Alternatively, in an example where the applied S1 force is too weak to achieve the second end position p2, the measuring S2 can be done by measuring the reaction force on the spring seat 23.

The present disclosure has mainly been described above with reference to a few embodiments. However, as is readily appreciated by a person skilled in the art, other embodiments than the ones disclosed above are equally possible within the scope of the present disclosure, as defined by the appended claims.

The invention claimed is:

1. A force measuring device comprising:

a spring module, comprising:

a test head defining an outer surface of the force measuring device;

a spring seat;

a spring arranged between the test head and the spring seat, with a first end of the spring engaging the test head and a second end of the spring engaging the spring seat; and a spring force adjustment arrangement comprising:

a lead screw axially fixed in relation to the test head;

and a spring cap directly engaged with the first end of the spring, the spring cap being screwed onto the lead screw and being axially movable and rotationally fixed in relation to the test head;

wherein the spring force adjustment arrangement is arranged to adjust an accumulated force of the spring and a longitudinal extension of the spring between the test head and the spring seat; and an electronic module, detachably mechanically connected to the spring module, the electronic module comprising:

a force sensor arranged in physical contact with the spring seat.

2. The force measuring device of claim 1, wherein the spring is a compression spring, a tension spring or a torsion spring.

3. The force measuring device of claim 1, wherein the test head is movable between a first end position and a second end position during elastic deformation of the spring.

4. The force measuring device of claim 3, the spring module further comprising a rigid element fixed in relation to the test head and arranged to be in contact with the spring seat at the second end position.

5. The force measuring device of claim 4, wherein the rigid element is a rod-shaped component.

6. The force measuring device of claim 1, wherein the spring module comprises a head joint fixed in relation to the test head and a spring cover fixed in relation to the spring seat.

7. The force measuring device of claim 6, wherein the spring cover and the head joint are telescopically arranged, allowing the head joint to be movable in relation to the spring cover in a longitudinal direction.

8. The force measuring device of claim 6, wherein the test head is detachably connected to the head joint via a bayonet connector, a screw thread, and/or a snap-fit connector.

9. The force measuring device of claim 1, wherein the device comprises a rear housing and a front housing, wherein the electronic module is arranged within the rear housing, wherein the spring module is arranged within the front housing, wherein an opening is arranged in a wall of the rear housing, wherein a counter opening is arranged in a wall of the front housing, wherein the force sensor is in physical contact with the spring seat though the opening and the counter opening, and wherein the rear housing is detachably connected to the front housing via a bayonet connector, a screw thread connector, and/or a snap-fit connector.

10. A method for measuring an external force applied by a user to the test head of the force measuring device of claim 1, the method comprising:

the user applying a force to the test head; and the sensor measuring a first part of the applied force, said first part being transmitted to the spring seat via the spring.

11. The method of claim 10, wherein the test head is moved from a first end position to a second end position by the force applied to the test head, during elastic deformation of the spring.

12. The method of claim 11, wherein, when the test head has reached the second end position, the measuring further comprises measuring a second part of the applied force, said second part being transmitted to the spring seat via a rigid element contacting the spring seat, said rigid element being fixed in relation to the test head.

13. A force measuring device comprising:

a rear and a front housing;

a spring module arranged within the front housing, comprising:

a test head defining an outer surface of the force measuring device;

a spring seat;

a spring arranged between the test head and the spring seat, with a first end of the spring engaging the test head and a second end of the spring engaging the spring seat; and a spring force adjustment arrangement arranged to adjust an accumulated force of the spring; and an electronic module arranged within the rear housing, detachably mechanically connected to the spring module, the electronic module comprising:

a force sensor arranged in physical contact with the spring seat;

wherein an opening is arranged in a wall of the rear housing;

wherein a counter opening is arranged in a wall of the front housing;

wherein the force sensor is in physical contact with the spring seat though the opening and the counter opening; and wherein the rear housing is detachably connected to the front housing via a bayonet connector, a screw thread connector, and/or a snap-fit connector.

* * * * *